(12) United States Patent
Robinson et al.

(10) Patent No.: US 9,474,638 B2
(45) Date of Patent: Oct. 25, 2016

(54) REINFORCED VALVE

(71) Applicant: Merit Medical Systems, Inc., South Jordan, UT (US)

(72) Inventors: Thomas Robinson, Addison, TX (US); Richard A. Brotherton, Park City, UT (US); Michelle Chatterton, Midvale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/196,012

(22) Filed: Mar. 4, 2014

(65) Prior Publication Data

US 2014/0257461 A1    Sep. 11, 2014

Related U.S. Application Data

(60) Provisional application No. 61/772,929, filed on Mar. 5, 2013.

(51) Int. Cl.
*A61F 2/06* (2013.01)
*A61F 2/91* (2013.01)
*A61F 2/04* (2013.01)
(Continued)

(52) U.S. Cl.
CPC . *A61F 2/91* (2013.01); *A61F 2/04* (2013.01); *A61F 2/07* (2013.01); *A61F 2/24* (2013.01); *A61F 2/2418* (2013.01); *A61F 2002/044* (2013.01); *Y10T 29/49405* (2015.01)

(58) Field of Classification Search
CPC .......... A61F 2/04; A61F 2/06; A61F 2/2412; A61F 2/2418; A61F 2002/044
USPC ................ 623/1.24, 1.26, 2.14, 2.18, 23.64, 623/23.65, 23.68
See application file for complete search history.

(56) References Cited

U.S. PATENT DOCUMENTS

| 5,061,275 A | 10/1991 | Wallsten et al. |
| 5,152,797 A * | 10/1992 | Luckman et al. ......... 623/20.16 |
| 5,314,473 A * | 5/1994 | Godin ....................... A61F 2/04 623/23.68 |

(Continued)

FOREIGN PATENT DOCUMENTS

| CN | 1433818 | 8/2003 |
| CN | 201200504 | 3/2009 |

(Continued)

OTHER PUBLICATIONS

International Search Report and Written Opinion dated Jun. 10, 2014 for PCT/US2014/020187.

(Continued)

*Primary Examiner* — Alvin Stewart
(74) *Attorney, Agent, or Firm* — Stoel Rives LLP

(57) ABSTRACT

The embodiments disclosed herein relate to a valve that is configured to be coupled to a stent. The valve may include a body, a rim, and an opening. The opening may include three or more leaflets that are configured to open and close. The valve may further include a reinforcement member that may be coupled to the rim. The reinforcement member may be formed of a mesh or mesh-like material or may be made of a polymeric film. The reinforcement member may aid in preventing a stitching element from tearing through the rim of the valve and may be coupled to the inner diameter or the outer diameter of the rim. The reinforcement member may also be molded within the rim.

18 Claims, 10 Drawing Sheets

(51) Int. Cl.
    *A61F 2/24*  (2006.01)
    *A61F 2/07*  (2013.01)

(56) References Cited

U.S. PATENT DOCUMENTS

| | | | |
|---|---|---|---|
| 5,607,445 A | 3/1997 | Summers | |
| 5,662,713 A | 9/1997 | Andersen et al. | |
| 5,766,263 A * | 6/1998 | Grundei et al. | 623/23.15 |
| 5,827,321 A | 10/1998 | Roubin et al. | |
| 5,833,707 A | 11/1998 | McIntyre et al. | |
| 5,843,175 A | 12/1998 | Frantzen | |
| 6,221,091 B1 * | 4/2001 | Khosravi | 606/200 |
| 6,254,642 B1 * | 7/2001 | Taylor | 623/23.64 |
| 6,264,700 B1 * | 7/2001 | Kilcoyne | A61F 2/04 623/23.68 |
| 6,302,917 B1 | 10/2001 | Dua et al. | |
| 6,348,065 B1 | 2/2002 | Brown et al. | |
| 6,464,720 B2 | 10/2002 | Boatman et al. | |
| 6,511,505 B2 | 1/2003 | Cox et al. | |
| 6,544,291 B2 | 4/2003 | Taylor | |
| 6,635,082 B1 | 10/2003 | Hossainy et al. | |
| 6,669,724 B2 | 12/2003 | Park et al. | |
| 6,701,174 B1 * | 3/2004 | Krause et al. | 600/407 |
| 6,764,518 B2 * | 7/2004 | Godin | A61F 2/04 623/23.68 |
| 6,845,776 B2 | 1/2005 | Stack et al. | |
| 6,878,162 B2 | 4/2005 | Bales et al. | |
| 6,913,619 B2 | 7/2005 | Brown et al. | |
| 6,929,658 B1 | 8/2005 | Freidberg et al. | |
| 6,966,928 B2 * | 11/2005 | Fell et al. | 623/14.12 |
| 6,991,647 B2 | 1/2006 | Jadhav | |
| 7,182,788 B2 * | 2/2007 | Jung | A61F 2/07 623/23.68 |
| 7,211,114 B2 * | 5/2007 | Bessler | A61F 2/07 623/23.65 |
| 7,462,192 B2 | 12/2008 | Norton et al. | |
| 7,488,347 B1 * | 2/2009 | Goble et al. | 623/18.11 |
| 7,547,321 B2 | 6/2009 | Silvestri et al. | |
| 7,608,114 B2 * | 10/2009 | Levine | A61B 17/0401 623/23.65 |
| 7,637,942 B2 | 12/2009 | Mangiardi et al. | |
| 7,641,694 B1 * | 1/2010 | Goble et al. | 623/18.11 |
| 7,695,446 B2 * | 4/2010 | Levine | A61B 17/0401 604/8 |
| 7,722,624 B2 | 5/2010 | Boucher et al. | |
| 7,837,645 B2 * | 11/2010 | Bessler | A61F 2/07 604/8 |
| 8,029,557 B2 * | 10/2011 | Sobrino-Serrano | A61F 2/04 623/1.24 |
| 8,114,045 B2 * | 2/2012 | Surti | A61F 5/0079 604/9 |
| 8,361,147 B2 * | 1/2013 | Shterling et al. | 623/14.12 |
| 8,500,821 B2 * | 8/2013 | Sobrino-Serrano | A61F 2/04 604/9 |
| 8,523,936 B2 | 9/2013 | Schmid et al. | |
| 8,579,985 B2 * | 11/2013 | Podolsky et al. | 623/22.42 |
| 8,597,366 B2 * | 12/2013 | Shank | A61F 2/07 623/23.68 |
| 8,632,600 B2 * | 1/2014 | Zannis et al. | 623/20.17 |
| 8,986,368 B2 | 3/2015 | Gill et al. | |
| 2002/0032479 A1 | 3/2002 | Hankh et al. | |
| 2002/0068967 A1 | 6/2002 | Drasler et al. | |
| 2002/0107565 A1 * | 8/2002 | Greenhalgh | 623/1.24 |
| 2002/0116052 A1 | 8/2002 | Cox et al. | |
| 2002/0138135 A1 | 9/2002 | Duerig et al. | |
| 2003/0009236 A1 * | 1/2003 | Godin | A61F 2/04 623/23.68 |
| 2003/0060884 A1 * | 3/2003 | Fell et al. | 623/14.12 |
| 2003/0109878 A1 * | 6/2003 | Grundei | 606/53 |
| 2003/0220700 A1 * | 11/2003 | Hammer et al. | 623/23.58 |
| 2004/0019374 A1 | 1/2004 | Hojeibane et al. | |
| 2004/0044401 A1 | 3/2004 | Bales et al. | |
| 2004/0068324 A1 * | 4/2004 | Grundei | 623/32 |
| 2004/0088040 A1 | 5/2004 | Mangiardi et al. | |
| 2004/0102866 A1 * | 5/2004 | Harris et al. | 700/117 |
| 2004/0107004 A1 * | 6/2004 | Levine et al. | 623/23.64 |
| 2004/0116996 A1 | 6/2004 | Freitag | |
| 2004/0127973 A1 | 7/2004 | Mangiardi et al. | |
| 2004/0204749 A1 | 10/2004 | Gunderson | |
| 2004/0236424 A1 * | 11/2004 | Berez et al. | 623/14.12 |
| 2005/0033424 A1 * | 2/2005 | Fell | 623/14.12 |
| 2005/0080491 A1 * | 4/2005 | Levine | A61B 17/0401 623/23.65 |
| 2005/0102038 A1 * | 5/2005 | Grundei | 623/32 |
| 2005/0112397 A1 * | 5/2005 | Rolfe et al. | 428/593 |
| 2005/0143745 A1 * | 6/2005 | Hodorek et al. | 606/87 |
| 2005/0168460 A1 * | 8/2005 | Razdan et al. | 345/419 |
| 2005/0169893 A1 * | 8/2005 | Koblish et al. | 424/93.7 |
| 2005/0183731 A1 | 8/2005 | Hunter et al. | |
| 2006/0157543 A1 * | 7/2006 | Abkowitz et al. | 228/233.2 |
| 2006/0212052 A1 | 9/2006 | Shin et al. | |
| 2006/0253190 A1 | 11/2006 | Kuo | |
| 2006/0259137 A1 * | 11/2006 | Artof et al. | 623/2.18 |
| 2006/0276874 A1 * | 12/2006 | Wilson et al. | 623/1.13 |
| 2007/0050011 A1 | 3/2007 | Klein et al. | |
| 2007/0050021 A1 | 3/2007 | Johnson | |
| 2007/0100437 A1 | 5/2007 | Welborn et al. | |
| 2007/0112437 A1 | 5/2007 | Shank | |
| 2007/0150049 A1 | 6/2007 | Nissl | |
| 2007/0173946 A1 * | 7/2007 | Bonutti | 623/20.14 |
| 2007/0198022 A1 * | 8/2007 | Lang et al. | 606/88 |
| 2007/0198097 A1 * | 8/2007 | Zegdi | 623/23.68 |
| 2007/0239273 A1 | 10/2007 | Allen | |
| 2007/0255412 A1 * | 11/2007 | Hajaj et al. | 623/17.11 |
| 2007/0276463 A1 | 11/2007 | Nissl et al. | |
| 2008/0004688 A1 | 1/2008 | Spenser et al. | |
| 2008/0030497 A1 * | 2/2008 | Hu et al. | 345/419 |
| 2008/0097579 A1 | 4/2008 | Shanley et al. | |
| 2008/0132998 A1 | 6/2008 | Mangiardi et al. | |
| 2008/0133020 A1 * | 6/2008 | Blackwell et al. | 623/20.34 |
| 2008/0140181 A1 | 6/2008 | Reynolds et al. | |
| 2008/0154351 A1 | 6/2008 | Leewood et al. | |
| 2008/0200979 A1 | 8/2008 | Dieck et al. | |
| 2008/0221664 A1 | 9/2008 | Bales et al. | |
| 2008/0221670 A1 | 9/2008 | Clerc | |
| 2008/0243225 A1 | 10/2008 | Satasiya et al. | |
| 2008/0255678 A1 * | 10/2008 | Cully | A61F 2/04 623/23.65 |
| 2008/0288044 A1 | 11/2008 | Osborne | |
| 2009/0036976 A1 | 2/2009 | Beach et al. | |
| 2009/0043373 A1 | 2/2009 | Arnault de la Menardiere et al. | |
| 2009/0105809 A1 | 4/2009 | Lee et al. | |
| 2009/0118830 A1 * | 5/2009 | Fell | 623/14.12 |
| 2009/0171465 A1 | 7/2009 | Bucay-Couto et al. | |
| 2009/0187240 A1 | 7/2009 | Clerc | |
| 2010/0004728 A1 | 1/2010 | Rao et al. | |
| 2010/0036504 A1 | 2/2010 | Sobrino-Serrano et al. | |
| 2010/0049313 A1 | 2/2010 | Alon et al. | |
| 2010/0082093 A1 | 4/2010 | Weber | |
| 2010/0114327 A1 | 5/2010 | Sobrino-Serrano | |
| 2010/0121461 A1 * | 5/2010 | Sobrino-Serrano | A61F 2/04 623/23.68 |
| 2010/0121462 A1 | 5/2010 | Sobrino-Serrano et al. | |
| 2010/0137998 A1 | 6/2010 | Sobrino-Serrano et al. | |
| 2010/0173066 A1 | 7/2010 | Mangiardi et al. | |
| 2010/0256744 A1 | 10/2010 | Laborde et al. | |
| 2010/0286760 A1 | 11/2010 | Beach et al. | |
| 2011/0004290 A1 | 1/2011 | Bales, Jr. et al. | |
| 2011/0054592 A1 | 3/2011 | Fliedner | |
| 2011/0160836 A1 * | 6/2011 | Behan | A61F 2/04 623/1.11 |
| 2011/0190874 A1 | 8/2011 | Celermajer et al. | |
| 2011/0190905 A1 * | 8/2011 | Behan | A61F 5/0079 623/23.68 |
| 2011/0265908 A1 | 11/2011 | Clerc | |
| 2012/0010697 A1 | 1/2012 | Shin et al. | |
| 2012/0059486 A1 | 3/2012 | Sobrino-Serrano et al. | |
| 2012/0071987 A1 | 3/2012 | Levy | |
| 2012/0108889 A1 * | 5/2012 | Behan | A61F 2/0009 600/30 |
| 2012/0310138 A1 * | 12/2012 | Behan | A61F 5/0079 604/9 |
| 2013/0006382 A1 | 1/2013 | Behan | |

(56) References Cited

U.S. PATENT DOCUMENTS

| | | | | |
|---|---|---|---|---|
| 2014/0257461 A1* | 9/2014 | Robinson | ............... | A61F 2/04 623/1.15 |
| 2014/0350694 A1* | 11/2014 | Behan | ............... | A61F 2/04 623/23.65 |
| 2015/0258253 A1* | 9/2015 | Fater | ............... | A61L 31/10 623/9 |

FOREIGN PATENT DOCUMENTS

| | | |
|---|---|---|
| EP | 1870057 | 12/2007 |
| EP | 2329796 | 6/2011 |
| EP | 2489331 | 8/2012 |
| EP | 2489331 | 10/2012 |
| WO | WO2005/089672 | 9/2005 |
| WO | WO2006/047520 | 5/2006 |
| WO | WO2006/069094 | 6/2006 |
| WO | 2009153768 | 12/2009 |
| WO | WO2010/098857 | 9/2010 |
| WO | WO2011/104269 | 9/2011 |
| WO | WO 2012/103501 | 8/2012 |

OTHER PUBLICATIONS

Office Action dated Jun. 19, 2014 for U.S. Appl. No. 13/153,150.
Office Action dated May 15, 2013 for U.S. Appl. No. 13/285,358.
Restriction Requirement dated May 6, 2014 for U.S. Appl. No. 13/909,427.
International Search Report and Written Opinion dated Jul. 1, 2014 for PCT/US2014/022328.
Office Action dated Oct. 17, 2014 for U.S. Appl. No. 13/909,427.
International Search Report and Written Opinion dated Mar. 29, 2013 for PCT/US2012/060364.
Material Safety Data Sheet, © 2010 Polymer Systems Technology Limited™, UK & Ireland Distributor, Nusil Silicone Technology. Effective Feb. 8, 2010, pp. 1-9.
International Search Report and Written Opinion dated Aug. 16, 2012 for PCT/US2012/035851.
Office Action dated Nov. 6, 2012 for U.S. Appl. No. 13/153,150.
Office Action dated Apr. 18, 2013 for U.S. Appl. No. 13/153,150.
International Search Report and Written Opinion dated Sep. 13, 2013 for PCT/US2013/044013.
Office Action dated Jan. 6, 2014 for U.S. Appl. No. 13/285,358.
Office Action dated Jan. 13, 2015 for U.S. Appl. No. 13/153,150.
Office Action dated Jan. 29, 2015 for U.S. Appl. No. 13/352,926.
European Search Report dated Feb. 18, 2015 for EP12793791.0.
International Search Report and Written Opinion dated May 15, 2014 for PCT/US2012/060364.
International Search Report and Written Opinion dated Oct. 16, 2012 for PCT/US2012/060364.
Notice of Allowance dated Dec. 23, 2014 for U.S. Appl. No. 13/285,358.
Office Action dated Apr. 9, 2015 for U.S. Appl. No. 14/202,128.
Office Action dated Jun. 19, 2014 for U.S. Appl. No. 13/352,926.
Office Action dated Jun. 30, 2015 for U.S. Appl. No. 13/909,427.
Office Action dated Sep. 10, 2015 for U.S. Appl. No. 13/153,150.
Extended European Search Report dated Jul. 22, 2016 for EP14759720.7.
Office Action dated Mar. 22, 2016 for U.S. Appl. No. 14/661,562.
Office Action dated Mar. 29, 2016 for U.S. Appl. No. 14/202,128.
Office Action dated Apr. 27, 2016 for U.S. Appl. No. 13/153,150.
Office Action dated May 11, 2016 for U.S. Appl. No. 13/909,427.

* cited by examiner

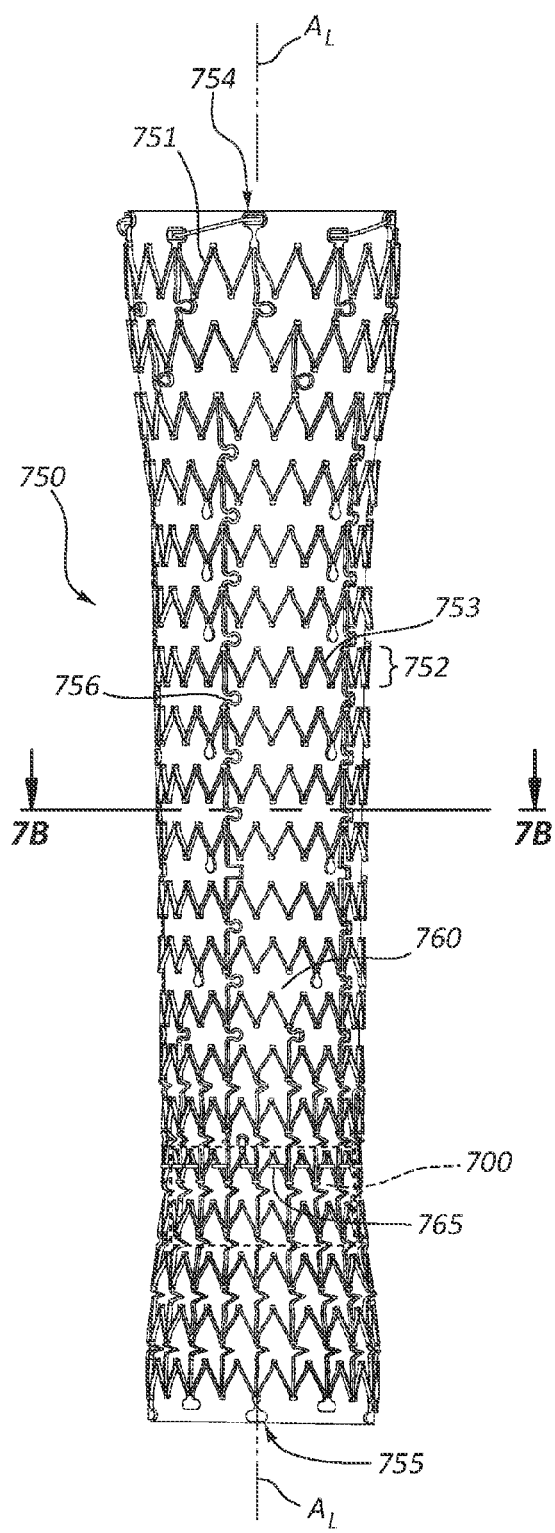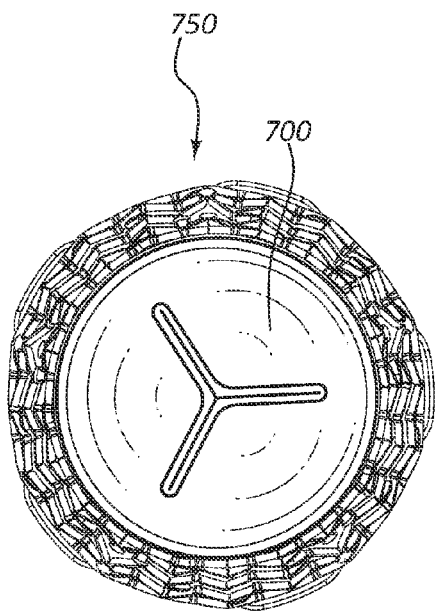
FIG. 7B
FIG. 7A

REINFORCED VALVE

RELATED APPLICATION

This application claims priority to U.S. Provisional Patent Application No. 61/772,929, titled REINFORCED VALVE, filed on Mar. 5, 2013, which is hereby incorporated herein by reference in its entirety.

TECHNICAL FIELD

The present disclosure relates generally to a valve that is to be used within a stent or similar implantable device. More particularly, the present disclosure relates to a valve which, in certain embodiments, comprises a reinforcement member.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 7A is a front view of a stent incorporating a valve, according to one embodiment of the present disclosure.

FIG. 7B is a cross-sectional view of the stent of FIG. 7A, taken along the view line 7B.

DETAILED DESCRIPTION

Figure 1A:
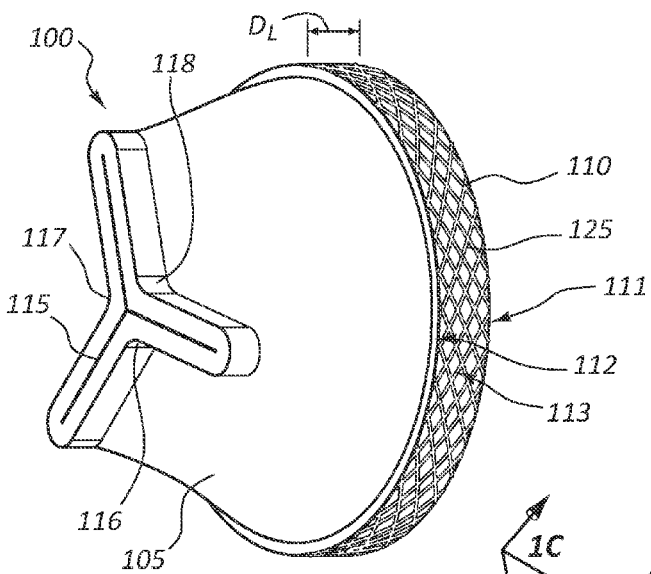
FIG. 1A is a perspective view of a valve, according to one embodiment of the present disclosure.

The various embodiments disclosed herein relate to a valve for placement in a body lumen. As set forth in more detail below, the valve may comprise a body, a rim, and an opening. In some embodiments, the opening may comprise three or more leaflets that are configured to open and close. The valve may further comprise a reinforcement member. The reinforcement member may be coupled to the inner diameter or the outer diameter of the rim of the valve. The reinforcement member may also be molded within the rim of the valve.

The reinforcement member may comprise a mesh or mesh-like material. The mesh or mesh-like material may comprise a network of individual threads or wires. The individual threads or wires may be formed of a tear-resistant material, such as a polymeric and/or metal material. In some embodiments, the reinforcement member may comprise a polymeric mesh. In other embodiments, the reinforcement member may comprise a metal mesh. In yet other embodiments, the reinforcement member may comprise a polymeric film.

Further disclosed herein are embodiments in which the valve may be coupled to the inner diameter or inner lumen of a stent or similar implantable device. In some embodiments, a stitching element such as a suture may be used. The stitching element may be configured such that it passes through a wall of the stent and through the rim of the valve. The stitching element may further pass through the reinforcement member. In some embodiments, the reinforcement member may aid in preventing the stitching element from tearing through the rim of the valve.

Though many of the examples provided herein refer to valves and stents configured for use within the esophagus, the present disclosure is also applicable to valves designed for a variety of other applications with stents or similar implantable devices configured to be disposed in various lumens of the body.

Embodiments may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal end of a medical device is the end nearest a practitioner during use, while the distal end is the opposite end. For example, in the case of a valve disposed within an esophageal stent—deployed through the mouth of a patient—the proximal end will be nearer the head of the patient and the distal end nearer the abdomen.

FIGS. 1A-1J are illustrative views of an embodiment of a valve 100 according to the present disclosure. As shown in FIG. 1A, the valve 100 may comprise a body 105, a rim 110, and an opening 115. The rim 110 may be disposed at a first end of the valve 100, and the opening 115 may be disposed at a second end of the valve 100. For example, in some embodiments the rim 110 may be disposed at a proximal end of the valve 100, and the opening 115 may be disposed at a distal end of the valve 100. The body 105 may be disposed such that it extends between the rim 110 and the opening 115.

The shape and size of the valve 100 may vary depending on the size of the stent for which the valve 100 is configured. For example, a relatively large stent may require a relatively large valve 100, whereas a relatively small stent may require a relatively small valve 100.

The valve 100 may be substantially conical or funnel-like in shape. For example, the rim 110 of the valve 100 may be substantially cylindrical in shape, and the body 105 may be configured such that it tapers inwardly as it extends from the rim 110 to the opening 115.

Other properties of the valve 100 may also be varied depending on the desired characteristics of the valve 100. For example, the thicknesses of the body 105, the rim 110, and the opening 115 may be varied to provide the valve 100 with a desired strength and flexibility. For example, greater thicknesses in the body 105, the rim 110, and the opening 115 may result in a relatively stiffer and stronger valve 100, whereas lesser thicknesses in the body 105, the rim 110, and the opening 115 may result in a relatively softer and weaker valve 100. Greater thicknesses in the body 105, the rim 110, and the opening 115 may also result in a relatively less flexible valve 100, whereas lesser thicknesses in the body 105, the rim 110, and the opening 115 may result in a relatively more flexible valve 100.

In some embodiments, the thickness of the body 105, the rim 110, and the opening 115 may vary in relation to each other. For example, in some embodiments, the thicknesses of the rim 110 and opening 115 may be greater than the thickness of the body 105. Configuring the valve 100 in this manner may provide added strength and support to the proximal and distal ends of the valve 100 while maintaining sufficient flexibility through the body 105. In other embodiments, the thicknesses of the body 105, the rim 110, and the opening 115 may be substantially the same.

In some embodiments, the rim 110 may be configured to provide strength and support to the valve 100. The rim 110 may also be configured to provide a location at which the valve 100 may be coupled to a stent. As shown in FIG. 1A, the rim 110 may comprise a wall 113 that comprises a proximal end 111 and a distal end 112. In some embodiments, the proximal end 111 may be disposed such that it is the most proximal end of the valve 100. As set forth in more detail below, the rim 110 may be coupled to a stent by a stitching element.

As further shown in FIG. 1A, the opening 115 may comprise three leaflets 116, 117, 118. However, additional leaflets are also contemplated. For example, in some embodiments, the opening 115 may comprise four, five, or six or more leaflets. In some embodiments, the leaflets 116, 117, 118 may be configured to open and close the valve 100. For example, the leaflets 116, 117, 118 may engage, coapt, or otherwise abut one another to close the valve 100. While the leaflets 116, 117, 118 engage, coapt, or otherwise abut one another, flow through the valve 100 may be restricted, and in some instances prohibited. The leaflets 116, 117, 118 may also be configured to disengage or otherwise separate from one another to open the valve 100. When the leaflets 116, 117, 118 are disengaged or separated, flow is allowed to pass through the valve 100. As set forth in more detail below, the leaflets 116, 117, 118 may be configured to open and close in response to various forces acting upon the valve 100.

The length of the leaflets 116, 117, 118 may affect their ability to engage, coapt, or otherwise abut one another to adequately close the valve 100. In some embodiments, the length of the leaflets 116, 117, 118 may be from about 1 mm to about 15 mm. In other embodiments, the length of the leaflets 116, 117, 118 may be from about 4 mm to about 11 mm. In yet other embodiments, the length of the leaflets 116, 117, 118 may be from about 7 mm to about 9 mm. The length of the leaflets 116, 117, 118 may also vary depending on the length of the valve 100. For example, a valve 100 that is about 19 mm long may comprise leaflets 116, 117, 118 that are about 7 mm long, and a valve 100 that is about 23 mm long may comprise leaflets 116, 117, 118 that are about 9 mm long. Other lengths may also be used.

The thickness of the leaflets 116, 117, 118 may also affect their ability to interact with one another to open and close the valve 100. In some embodiments, the thickness of the leaflets 116, 117, 118 may be from about 0.1 mm to about 3 mm. In other embodiments, the thickness of the leaflets 116, 117, 118 may be from about 0.5 mm to about 2.5 mm. In other embodiments, the thickness of the leaflets 116, 117, 118 may be from about 1.9 mm to about 2.3 mm. The thickness of the leaflets 116, 117, 118 may also vary depending on the length of the valve 100. For example, a valve 100 that is about 19 mm long may comprise leaflets 116, 117, 118 that are about 1.9 mm thick, and a valve 100 that is about 23 mm long may comprise leaflets 116, 117, 118 that are about 2.3 mm thick. Other thicknesses may also be used.

As further shown in FIG. 1A, the valve 100 may comprise a reinforcement member 125. The illustrated reinforcement member 125 may be representative of any mesh or mesh-like material, including fine and/or very fine mesh or mesh-like materials. The reinforcement member 125 may be coupled to the rim 110 of the valve 100. The reinforcement member 125 may be coupled to the rim 110 in a variety of ways. For example, in some embodiments, the reinforcement member 125 may be bonded or otherwise adhered to the rim 110 via a bonding or adhesive agent. In other embodiments, the reinforcement member 125 may be integral with the rim 110. For example, the reinforcement member 125 may be molded to the rim 110. The reinforcement member 125 may be either partially or completely molded within the rim 110. In still other embodiments, the reinforcement member 125 may be neither bonded to the rim 110 nor molded to or within the rim 110; rather, the reinforcement member 125 may be disposed adjacent to the rim 110 and thereafter coupled to the rim 110 via a stitching element. In some embodiments, the stitching element may also be used to couple the valve 100 to a stent.

The reinforcement member 125 may be coupled to the rim 110 in variety of locations. For example, as shown in FIG. 1A, the reinforcement member 125 may be coupled to the outer diameter of the rim 110. In other embodiments, the reinforcement member 125 may be coupled to the inner diameter of the rim 110. In yet other embodiments, the reinforcement member 125 may be coupled to neither the outer nor the inner diameter of the rim 110; rather, the reinforcement member 125 may be molded within the rim 110. In still other embodiments, the reinforcement member 125 may be only partially molded within the rim 110.

In some embodiments, one or more dimensions of the reinforcement member 125 may be constrained within one or more dimensions of the rim 110. For example, as shown in FIG. 1A, the reinforcement member 125 is disposed within the length $D_L$ of the rim 110. In some embodiments, the reinforcement member 125 may be disposed between the proximal end 111 and the distal end 112 of the rim 110. In some embodiments, the reinforcement member 125 may further be configured such that it does not extend beyond either the proximal end 111 or the distal end 112 of the rim 110. In other embodiments, the reinforcement member 125 need not be constrained within the length $D_L$ of the rim 110; rather, the reinforcement member 125 may be configured such that it may extend beyond either or both of the proximal end 111 and/or the distal end 112 of the rim 110.

The reinforcement member 125 may be made of a variety of materials. For example, in some embodiments, the reinforcement member 125 may comprise a mesh or mesh-like material. The mesh or mesh-like material may comprise a network of individual interconnected threads. In some embodiments, the threads may comprise a polymeric material.

The density or number of threads in the mesh or mesh-like material may vary as desired. In some embodiments, the density of the mesh or mesh-like material may be between about 135 and about 425 ends per inch (i.e., 135-425 mesh). In other embodiments, the density of the mesh or mesh-like material may be between about 185 and about 375 ends per inch (i.e., 185-375 mesh). In other embodiments, the density of the mesh or mesh-like material may be between about 235 and about 325 ends per inch (i.e., 235-325 mesh). In other embodiments, the density of the mesh or mesh-like material may be as low as 10 ends per inch (i.e., 10 mesh). Alternatively, the number of threads per inch could also be so great that the mesh or mesh-like material may be film-like or similar to a film. Further, as discussed below, in some embodiments, a film may be used.

In some embodiments, the mesh or mesh-like material may comprise a network of individual interconnected wires. The wires may comprise a metal material. For example, in some embodiments the wires may comprise a shape-memory metal such as Nitinol®. In some embodiments, the wires may comprise stainless steel. In yet other embodiments, the mesh or mesh-like material may comprise a combination of individual interconnected threads or wires comprising both metal and polymeric materials.

Additional types of reinforcement members 125 (e.g., not mesh or mesh-like materials) may be used. For example, in some embodiments, the reinforcement member 125 may comprise a polymeric film. The polymeric film may comprise a polymer having a greater tensile and/or tear strength than the material used in forming the body 105, the rim 110, and/or the opening 115 of the valve 100. Thus, the polymeric film may provide strength and reinforcement to the rim 110. In some embodiments, the reinforcement member 125 may further aid in keeping the stitching element from tearing through the rim 110 of the valve 100.

In some embodiments, the valve 100, including the reinforcement member 125, may be configured such that it is not irreparably damaged when it is coupled to a stent that is crimped by a deployment device. As such, in some embodiments, the valve 100, including the reinforcement member 125, may substantially retain its shape and structure after the stent to which the valve 100 is coupled is deployed from a deployment device. In some embodiments, the valve 100, including the reinforcement member 125, may substantially retain its shape and structure after being crimped inside a stent within a deployment device for a period of up to about 24 hours. In other embodiments, the valve 100, including the reinforcement member 125, may substantially retain its shape and structure after being crimped inside a stent within a deployment device for a period of up to about 12 hours. In yet other embodiments, the valve 100, including the reinforcement member 125, may substantially retain its shape and structure after being crimped inside a stent within a deployment device for a period of up to about six hours.

Figure 1B:
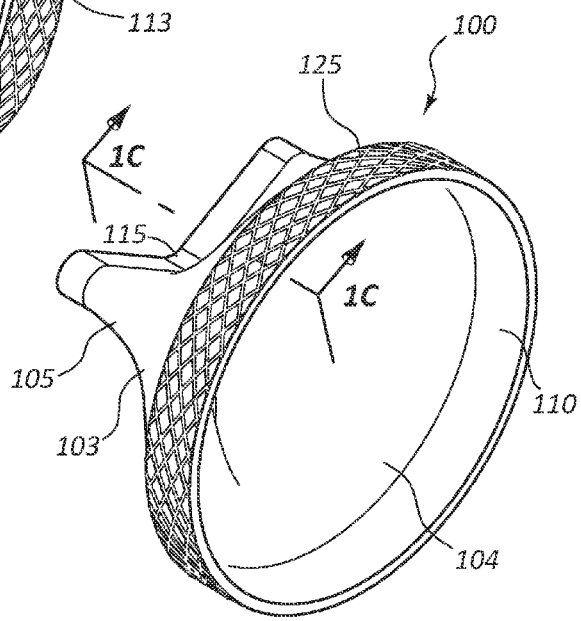
FIG. 1B is another perspective view of the valve of FIG. 1A.

FIG. 1B is another perspective view of the valve 100 of FIG. 1A showing a portion of the inside of the valve 100. As shown in FIG. 1B, the valve 100 may comprise a body 105, a rim 110, and an opening 115. The valve 100 may further comprise a reinforcement member 125 coupled to the outer diameter of the rim 110.

As further shown in FIG. 1B, the body 105 of the valve 100 may comprise an outer surface 103 and an inner surface 104. The outer surface 103 faces the outside of the valve 100 and may be configured such that it may be substantially convex. The inner surface 104 faces the inside of the valve 100 and may be configured such that it is substantially concave. The outer and inner surfaces 103, 104 may each be configured such that they are substantially smooth.

Figure 1C:
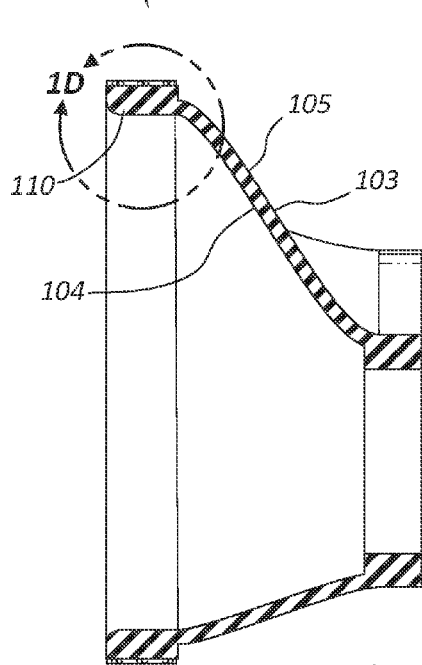
FIG. 1C is a cross-sectional view of a portion of the valve of FIG. 1B taken along the view line 1C.

FIG. 1C is a cross-sectional view of the valve 100 of FIG. 1B taken along line 1C. Many of the structural features and aspects of the valve 100 described above are further evident in this cross-sectional view. For example, as shown in FIG. 1C, the body 105 of the valve 100 may taper inwardly from the rim 110 to the opening 115. The nature of the outer and inner surfaces 103, 104 is also depicted. For example, the outer surface 103 may be substantially convex, while the inner surface 104 may be substantially concave.

The varying thicknesses of the body 105, the rim 110, and the opening 115 are further shown in FIG. 1C. As shown therein, the thicknesses of the rim 110 and opening 115 may be configured such that they are greater than the thickness of the body 105. Thus the valve 100 may be configured such that it has added structural strength and support in the rim 110 and the opening 115 while remaining relatively flexible in the body 105.

Figure 1D:
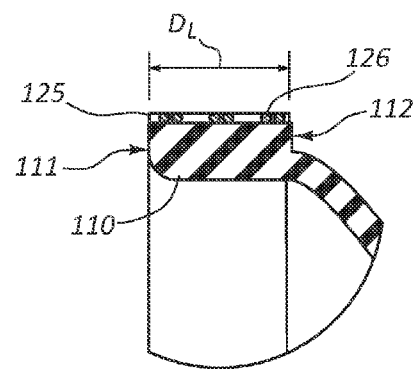
FIG. 1D is an enlarged view of a portion of the valve of FIG. 1C taken along the view line 1D.

FIG. 1D is a close-up of a portion of the cross-section of FIG. 1C. As shown therein, the reinforcement member 125 may be coupled to the outer diameter of the rim 110. As further shown, the reinforcement member 125 may be constrained within the rim 110 and may be disposed such that it does not extend beyond the proximal and distal ends 111, 112 of the rim 110. The reinforcement member 125 is further disposed such that it is within the length $D_L$ of the rim 110. FIG. 1D further shows a reinforcement member 125 comprising a mesh or mesh-like material that comprises individual threads or wires 126. As set forth above, these threads or wires 126 may be part of a network of threads or wires 126 that may interconnect to form the mesh or mesh-like material.

Figure 1E:
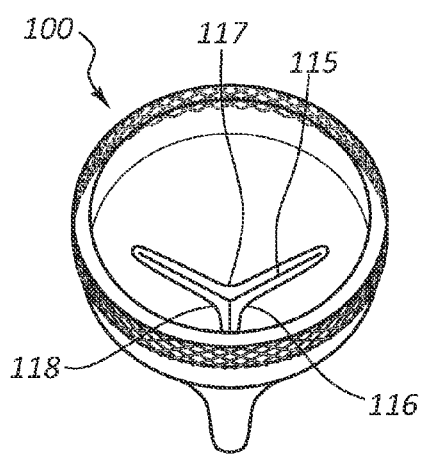
FIG. 1E is a perspective view of a valve in a closed configuration.
Figure 1F:
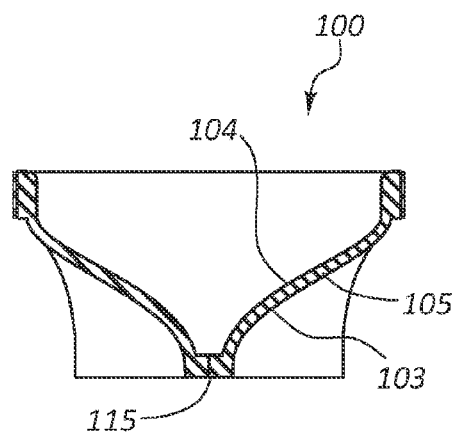
FIG. 1F is a cross-sectional view of a portion of the valve of FIG. 1E in a closed configuration.
Figure 1G:
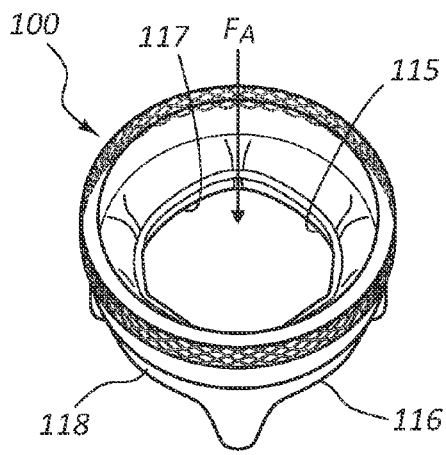
FIG. 1G is a perspective view of a valve in an antegrade open configuration.
Figure 1H:
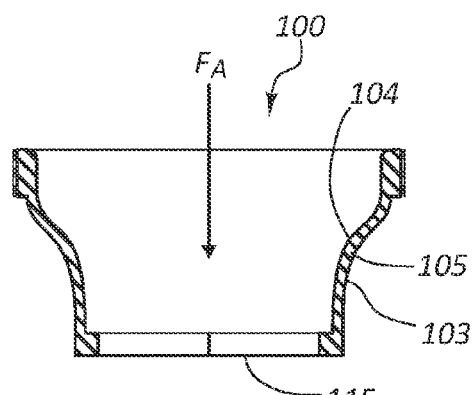
FIG. 1H is a cross-sectional view of a portion of the valve of FIG. 1G in an antegrade open configuration.
Figure 1I:
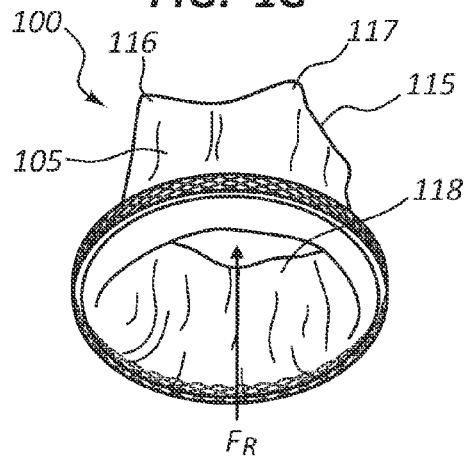
FIG. 1I is a perspective view of a valve in a retrograde open configuration.
Figure 1J:
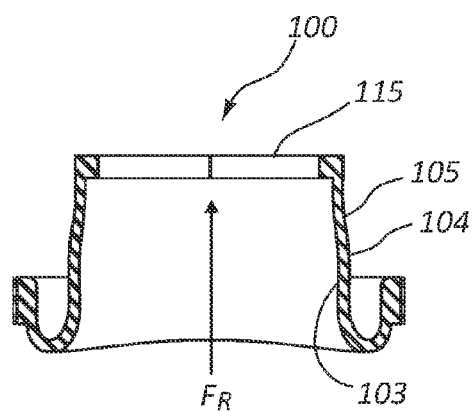
FIG. 1J is a cross-sectional view of a portion of the valve of FIG. 1I in a retrograde open configuration.

As shown in FIGS. 1E-1J, the valve 100 may be configured such that it is a two-way valve 100. Accordingly, the valve 100 may be configured to allow passage of flow in both the antegrade and retrograde directions (i.e., antegrade flow and retrograde flow). The valve 100 may have three primary configurations—a closed configuration (FIGS. 1E and 1F), an antegrade open configuration (FIGS. 1G and 1H), and a retrograde open configuration (FIGS. 1I and 1J).

FIGS. 1E and 1F show the valve 100 in a closed configuration. Specifically, FIG. 1E is a perspective view of the valve 100 in the closed configuration and FIG. 1F is a cross-sectional view of the valve 100 in the closed configuration. It is contemplated that the closed configuration is the normal configuration of the valve 100. Accordingly, the valve 100 may be configured such that it is in the closed configuration when it is at rest or otherwise substantially free from external forces in the antegrade and retrograde directions (i.e., antegrade force and retrograde force). The valve 100 may also be configured such that it is biased toward the closed configuration. As such, the valve 100 may return to the closed configuration after an external antegrade or retrograde force is removed from the valve 100.

As shown in FIGS. 1E and 1F, in the closed configuration, the opening 115 of the valve 100 is closed. In the closed configuration, the leaflets 116, 117, 118 may be configured to engage, coapt, or otherwise abut with one another to close the valve 100. Thus, flow through the valve 100 may be restricted, and in some instances prohibited, by the leaflets 116, 117, 118 when the valve 100 is in the closed configuration. As further shown in FIGS. 1E and 1F, when the valve 100 is in the closed configuration, the inner surface 104 of the body 105 may be substantially concave, and the outer surface 103 of the body 105 may be substantially convex.

FIGS. 1G and 1H show the valve in an antegrade open configuration. Specifically, FIG. 1G is a perspective view of the valve 100 in the antegrade open configuration and FIG. 1H is a cross-sectional view of the valve 100 in the antegrade open configuration. As shown in FIGS. 1G and 1H, in the antegrade open configuration, the opening 115 of the valve 100 is open. In the antegrade open configuration, the leaflets 116, 117, 118 may be configured such that they no longer engage, coapt, or otherwise abut one another like they do in the closed configuration. Rather, at least a portion of the leaflets 116, 117, 118 may be disengaged, spaced apart, or otherwise separated from one another.

The valve 100 may be opened to the antegrade open configuration in response to a force in the antegrade direction $F_A$ (i.e., an antegrade force). As an antegrade force $F_A$ is applied to the valve 100, the leaflets 116, 117, 118 may be forced outwardly thus allowing antegrade flow to pass through the opening 115 of the valve 100. As previously discussed, when the antegrade force $F_A$ is removed, the biasing of the valve 100 may cause the valve 100 to return to the closed configuration.

As further shown in FIGS. 1G and 1H, when the valve 100 is in the antegrade open configuration, the inner surface 104 of the body 105 may be substantially concave, and the outer surface 103 of the body 105 may be substantially convex.

FIGS. 1I and 1J show the valve 100 in the retrograde open configuration. Specifically, FIG. 1I is a perspective view of the valve 100 in the retrograde open configuration and FIG. 1J is a cross-sectional view of the valve 100 in the retrograde open configuration. As shown in FIGS. 1I and 1J, in the retrograde open configuration, the opening 115 of the valve 100 is open. In the retrograde open configuration, the leaflets 116, 117, 118 may be configured such that they no longer engage, coapt, or otherwise abut one another like they do in the closed configuration. Rather, at least a portion of the leaflets 116, 117, 118 may be disengaged, spaced apart, or otherwise separated from one another.

The valve 100 may be opened to the retrograde open configuration in response to a force in the retrograde direction $F_R$ (i.e., a retrograde force). As a retrograde force $F_R$ is applied to the valve 100, the leaflets 116, 117, 118 are initially pushed inwardly against one another. If the retrograde force $F_R$ is sufficiently strong, the body 105 and the leaflets 116, 117, 118 of the valve 100 may become inverted. Thus, as shown in FIGS. 1I and 1J, when the valve 100 is fully opened in response to the retrograde force $F_R$, the body 105 and the leaflets 116, 117, 118 may extend proximally, or upwardly, thereby allowing retrograde flow to pass through the valve 100. As further shown in FIGS. 1I and 1J, when the valve 100 is in the retrograde open configuration, the inner surface 104 of the body 105 is inverted such that it is substantially convex, and the outer surface 103 of the body 105 is inverted such that it is substantially concave. When the retrograde force $F_R$ is removed, the biasing of the valve 100 may cause the valve 100 to return to the closed configuration.

The valve 100 may transition from the closed configuration to the antegrade open configuration and back to the closed configuration without damaging any of the components of the valve 100. Similarly, the valve 100 may transition from the closed configuration to the retrograde open configuration and back to the closed configuration without damaging any of the components of the valve 100.

Different amounts of force may be required to transition the valve 100 from the closed configuration to the antegrade and retrograde open configurations. For example, the magnitude of the antegrade force $F_A$ required to transition the valve 100 from the closed configuration to the antegrade open configuration may be substantially less than the magnitude of retrograde force $F_R$ required to transition the valve 100 from the closed configuration to the retrograde open configuration.

In some embodiments the magnitude of the antegrade force $F_A$ required to transition the valve 100 to the antegrade open configuration may be relatively low, while the magnitude of retrograde force $F_R$ required to transition the valve 100 to the retrograde open configuration may be relatively high. The valve 100 may therefore be configured to easily allow flow to pass in the antegrade direction (i.e., antegrade flow), while substantially blocking flow from passing in the retrograde direction (i.e., retrograde flow). For example, in some embodiments, forces as low as 0.7 mmHg may be sufficient to transition the valve 100 from the closed configuration to the antegrade open configuration thereby allowing an antegrade flow rate of at least 140 ml/min. The valve 100 may also be configured such that it can withstand pressures of up to 30 mmHg or higher in the retrograde direction prior to transitioning from the closed configuration to the retrograde open configuration.

The amount of force required to transition the valve 100 from the closed configuration to the antegrade and retrograde open configurations may be controlled by varying the properties of the valve 100. For example, the material used to form the body 105, the rim 110, and the opening 115 may be varied to increase or decrease the forces required to transition or open the valve 100. In some embodiments, the amount of force required to transition or open the valve 100 may also be adjusted by varying the thicknesses of the body 105, the opening 115 and/or the leaflets 116, 117, 118. The length of the leaflets 116, 117, 118 may also be varied to change the amount of force required to transition or open the valve 100.

Figures 2A, 2B, 2C:
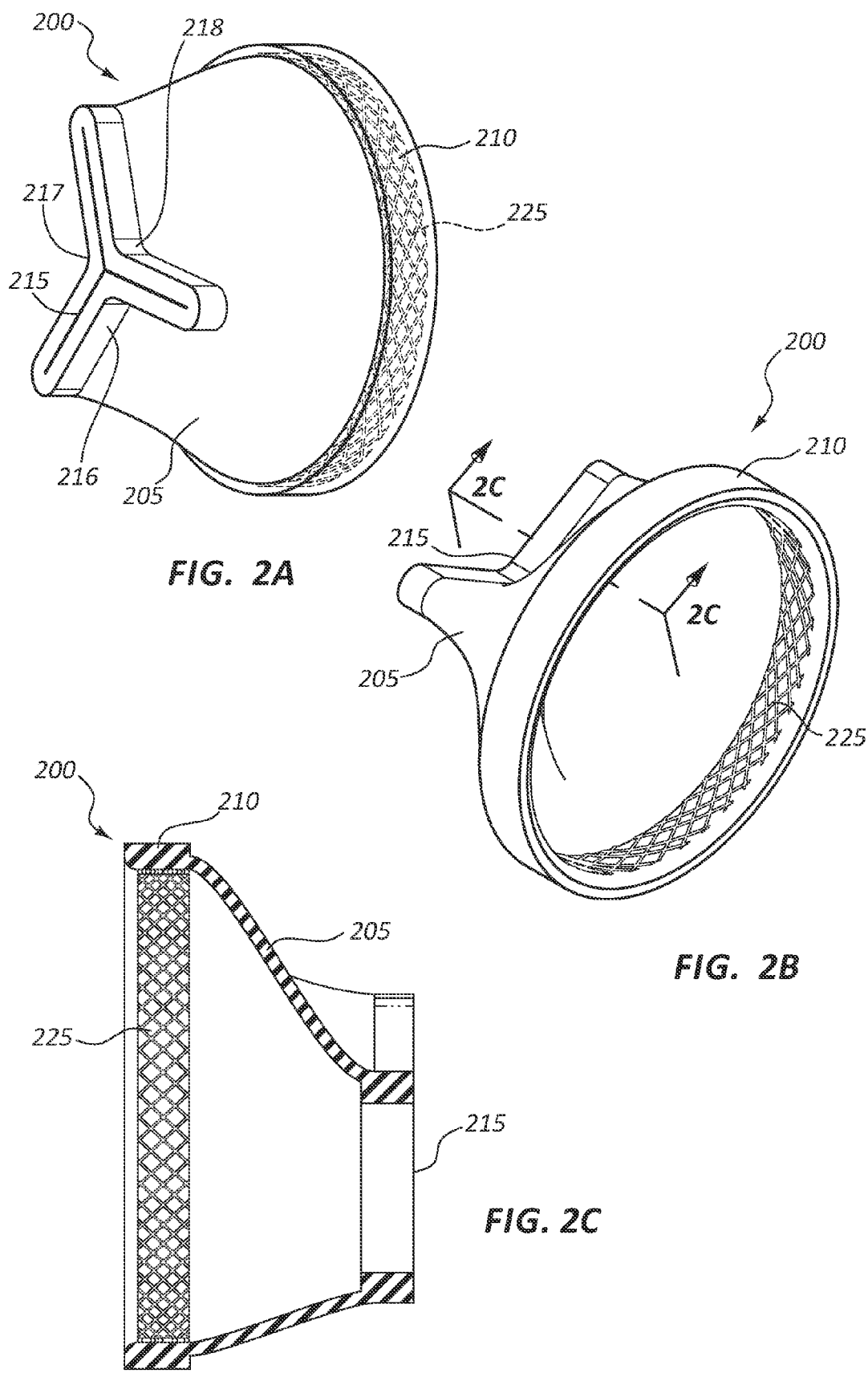
FIG. 2A is a perspective view of a valve, according to another embodiment of the present disclosure.
FIG. 2B is another perspective view of the valve of FIG. 2A.
FIG. 2C is a cross-sectional view of a portion of the valve of FIG. 2B taken along the view line 2C.

FIGS. 2A-2C are views of another embodiment of a valve 200 according to the present disclosure. The valve 200 can, in certain respects, resemble components of the valve 100 described in connection with FIGS. 1A-1J above. It will be appreciated that the illustrated embodiments may have analogous features. Accordingly, like features are designated with like reference numerals, with the leading digits incremented to "2." (For instance, the valve is designated "100" in FIG. 1, and an analogous valve is designated as "200" in FIG. 2.) Relevant disclosure set forth above regarding similarly identified features thus may not be repeated hereafter. Moreover, specific features of the valve 200 and related components shown in FIGS. 2A-2C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the valve of FIGS. 2A-2C. Any suitable combination of the features, and variations of the same, described with respect to the valve 100 and components illustrated in FIGS. 1A-1J, can be employed with the valve 200 and components of FIGS. 2A-2C, and vice versa. This pattern of disclosure applies equally to further embodiments depicted in subsequent figures and described hereafter.

As shown in FIGS. 2A-2C, the valve 200 may comprise a body 205, a rim 210, and an opening 215. The opening 215 may comprise three leaflets 216, 217, 218. As further illustrated, the valve 200 may further comprise a reinforcement member 225. In contrast to the reinforcement member 125 of FIGS. 1A-1J, the reinforcement member 225 of FIGS. 2A-2C may be coupled to the inner diameter of the rim 210. Coupling the reinforcement member 225 to the inner diameter of the rim 210 may be accomplished in any of the ways previously discussed. For example, the reinforcement member 225 may be bonded or molded to the inner diameter of the rim 210. The reinforcement member 225 may also be coupled to the inner diameter of the rim 210 by a stitching element.

Figures 3A, 3B, 3C:
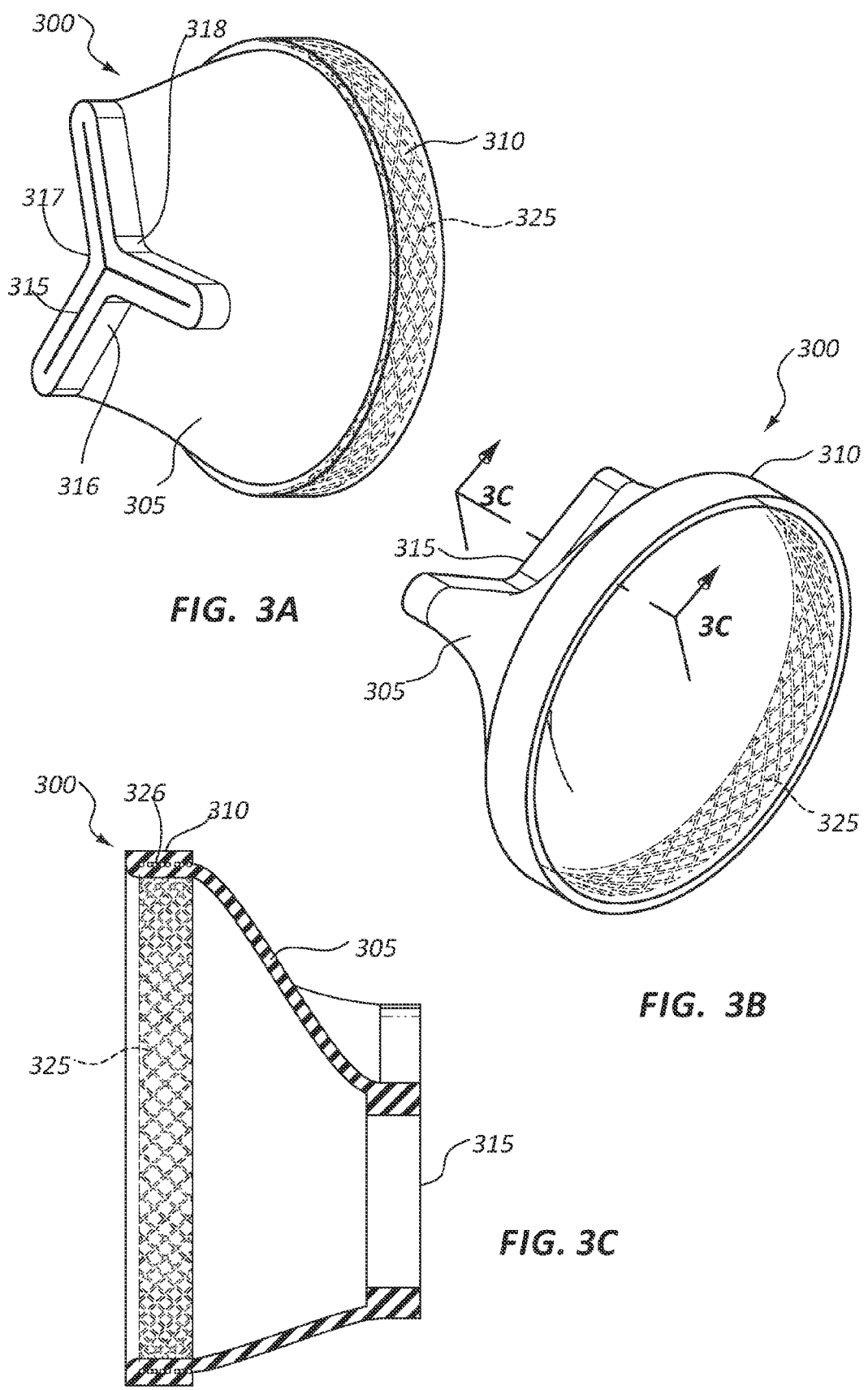
FIG. 3A is a perspective view of a valve, according to another embodiment of the present disclosure.
FIG. 3B is another perspective view of the valve of FIG. 3A.
FIG. 3C is a cross-sectional view of a portion of the valve of FIG. 3B taken along the view line 3C.

FIGS. 3A-3C show another embodiment of a valve 300 according to the present disclosure. As illustrated therein, the valve 300 may comprise a body 305, a rim 310, and an opening 315. The opening 315 may comprise three leaflets 316, 317, 318. As further illustrated in FIGS. 3A-3C, the valve 300 may further comprise a reinforcement member 325 coupled to the rim 310. In contrast to the reinforcement member 125 of FIGS. 1A-1J, the reinforcement member 325 may be coupled to the inside of the rim 310. As set forth above, the reinforcement member 325 may be coupled to the inside of the rim 310 by being molded within the rim 310. This is further shown in the cross-section of FIG. 3C, where each of the individual threads or wires 326 is disposed within the rim 310.

Figure 4A:
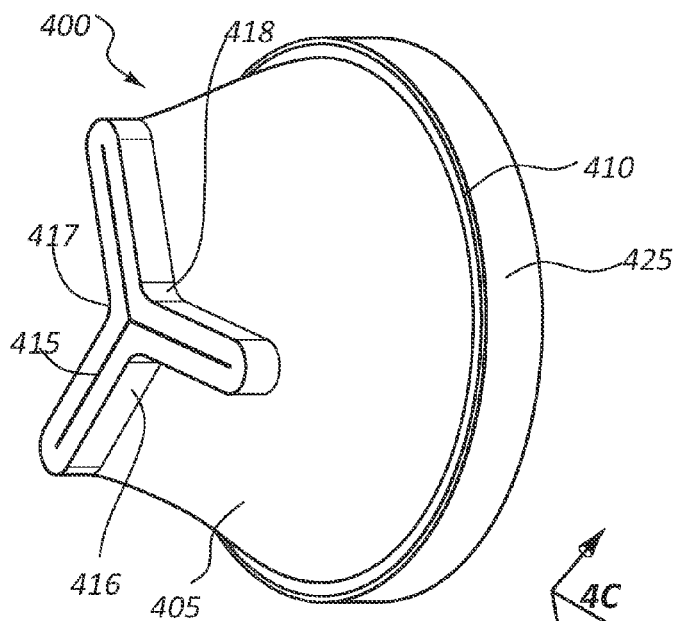
FIG. 4A is a perspective view of a valve, according to another embodiment of the present disclosure.
Figure 4B:
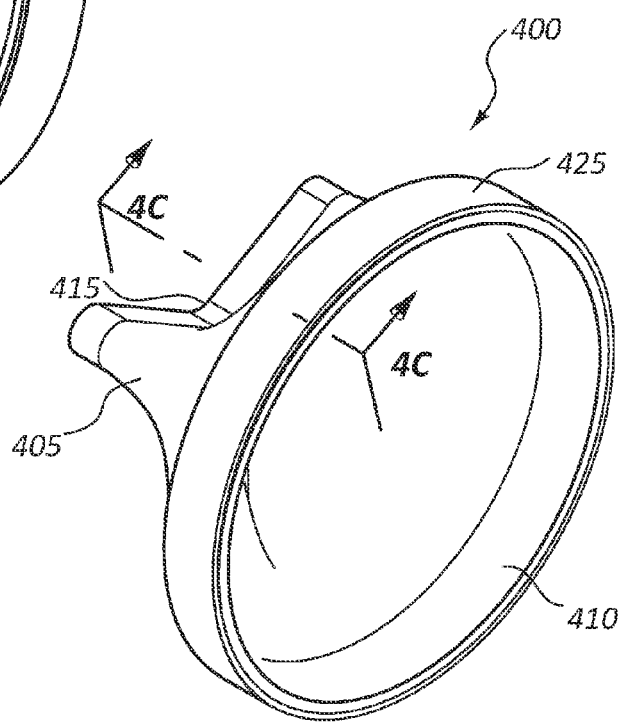
FIG. 4B is another perspective view of the valve of FIG. 4A.
Figure 4C:
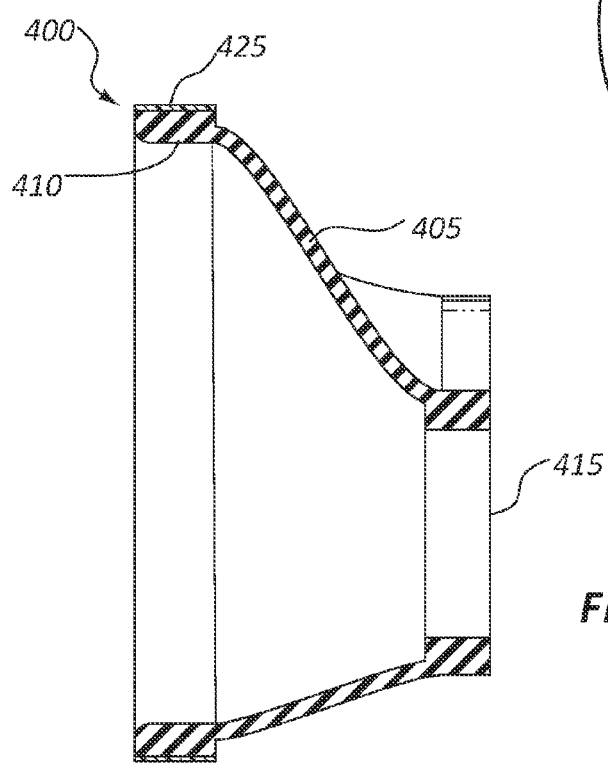
FIG. 4C is a cross-sectional view of a portion of the valve of FIG. 4B taken along the view line 4C.

FIGS. 4A-4C show yet another embodiment of a valve 400 according to the present disclosure. As illustrated therein, the valve 400 may comprise a body 405, a rim 410, and an opening 415. The opening 415 may comprise three leaflets 416, 417, 418. The valve 400 may further comprise a reinforcement member 425 coupled to the rim 410. As shown in FIGS. 4A-4C, the reinforcement member 425 may comprise a polymeric film. As further shown in FIGS. 4A-4C, the polymeric film may be coupled to the outer diameter of the rim 410.

Figures 5A, 5B, 5C:
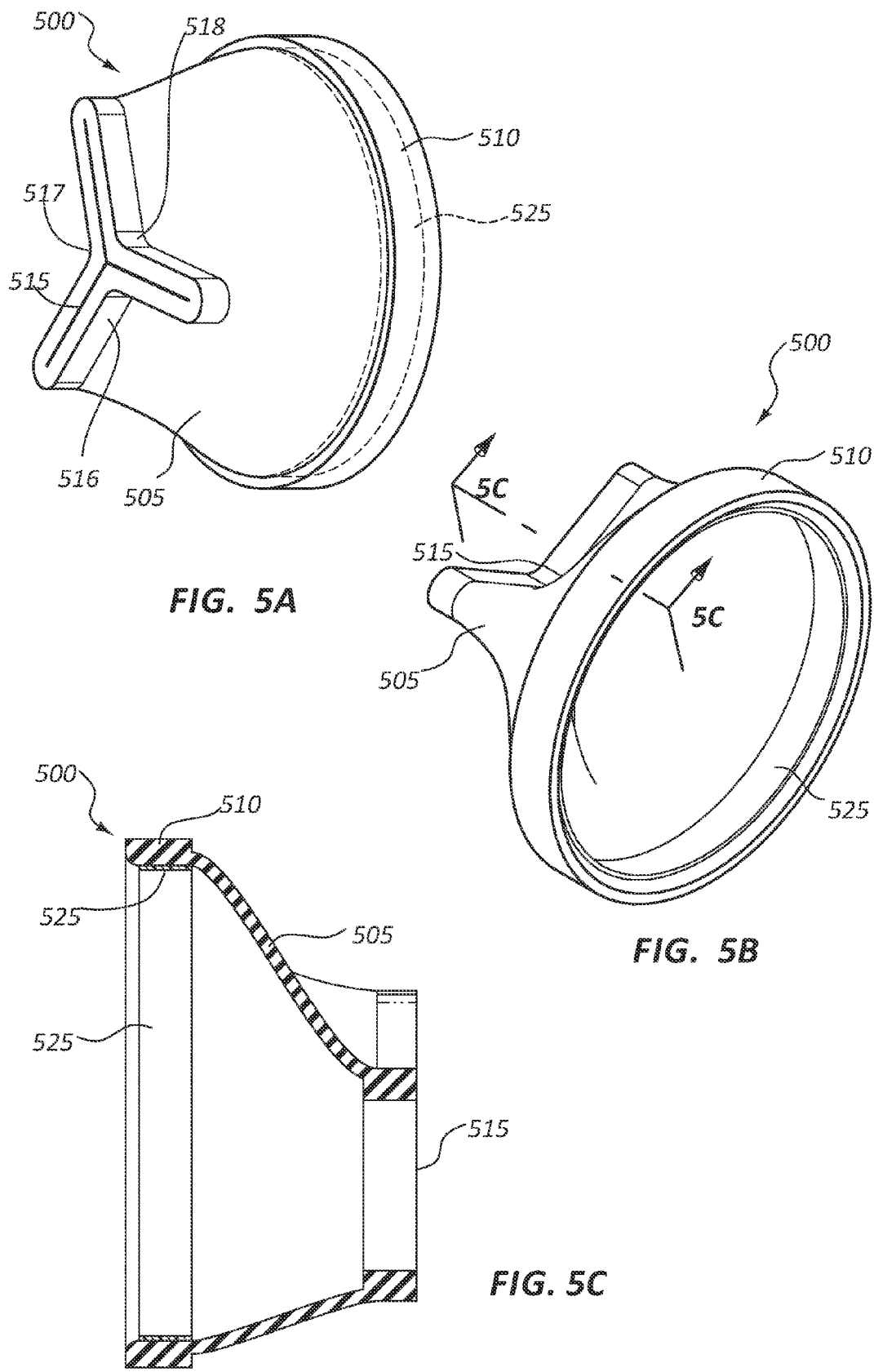
FIG. 5A is a perspective view of a valve, according to another embodiment of the present disclosure.
FIG. 5B is another perspective view of the valve of FIG. 5A.
FIG. 5C is a cross-sectional view of a portion of the valve of FIG. 5B taken along the view line 5C.

FIGS. 5A-5C show yet another embodiment of a valve 500 according to the present disclosure. As illustrated therein, the valve 500 may comprise a body 505, a rim 510, and an opening 515. The opening 515 may comprise three leaflets 516, 517, 518. The valve 500 may further comprise a reinforcement member 525 coupled to the rim 510. As further shown in FIGS. 5A-5C, the reinforcement member 525 may comprise a polymeric film. In contrast to the embodiment of FIGS. 4A-4C, the polymeric film in FIGS. 5A-5C may be coupled to the inner diameter of the rim 510.

Figure 6A:
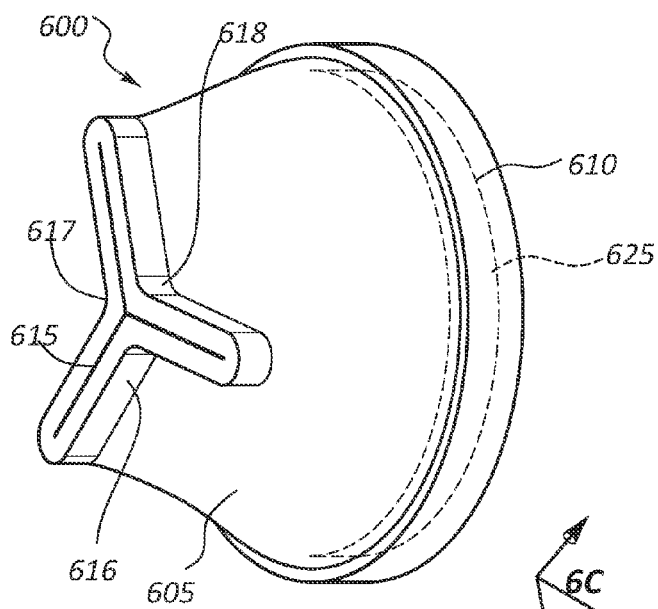
FIG. 6A is a perspective view of a valve, according to another embodiment of the present disclosure.
Figure 6B:
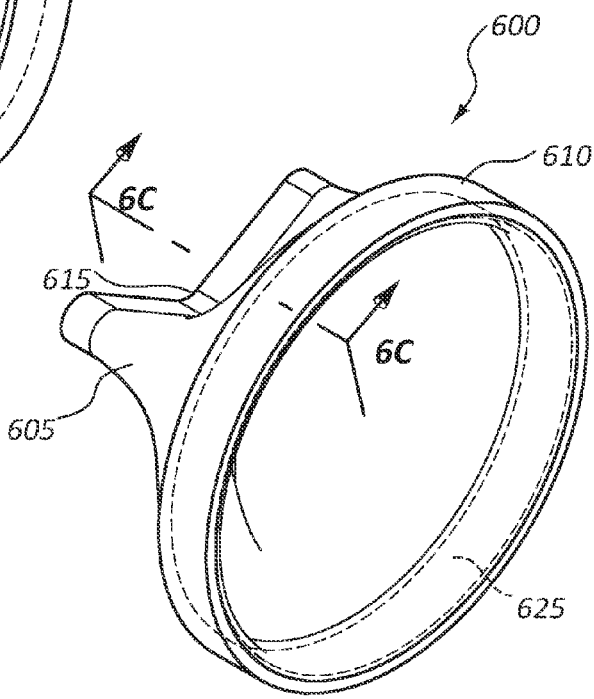
FIG. 6B is another perspective view of the valve of FIG. 6A.
Figure 6C:
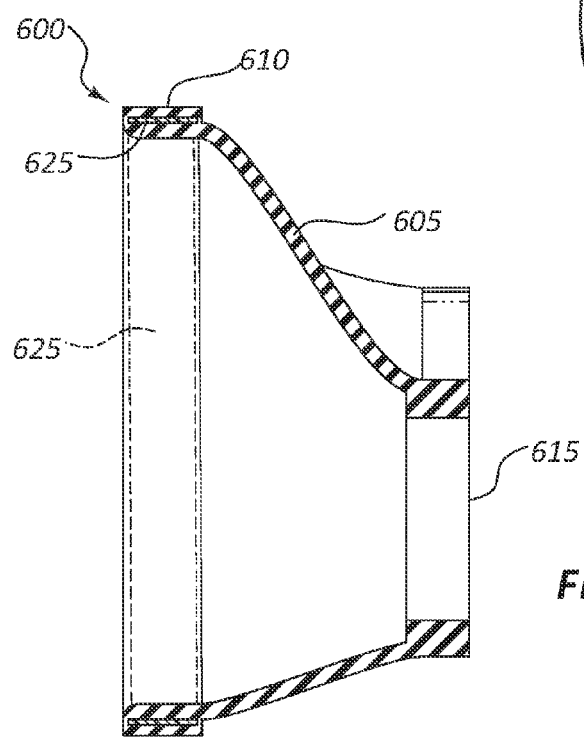
FIG. 6C is a cross-sectional view of a portion of the valve of FIG. 6B taken along the view line 6C.

FIGS. 6A-6C show yet another embodiment of a valve 600 according to the present disclosure. As illustrated therein, the valve 600 may comprise a body 605, a rim 610, and an opening 615. The opening 615 may comprise three leaflets 616, 617, 618. The valve 600 may further comprise a reinforcement member 625 coupled to the rim 610. As further shown in FIGS. 6A-6C, the reinforcement member 625 may comprise a polymeric film. In contrast to the embodiment of FIGS. 4A-4C, the polymeric film in FIGS. 6A-6C may be coupled to or otherwise disposed within the inside of the rim 610. As set forth above, the reinforcement member 625 may be coupled or otherwise disposed to the inside of the rim 610 by being molded within the rim 610.

Disclosed herein are also embodiments in which the valve is coupled to a stent or similar implantable device. For example, the valve may be coupled to an esophageal stent. An esophageal stent may be an implantable device configured for placement in a lumen of the esophagus to treat, for example, a stricture, a closure, a blockage or an occlusion of the esophagus. The esophageal stent may be configured to resist stricture and otherwise function to maintain patency of the esophagus. Additionally, the stent may comprise a variety of components, and the parameters of these components (e.g., shape, length, thickness, position, etc.) may be configured to provide the stent with certain properties. For example, the stent may be configured to distribute transverse loads or to change shape in response to certain forces.

Referring to FIG. 7A, a side view of a stent 750 configured with a valve 700 according to the present disclosure, the stent 750 may be formed of a suitable material configured with a scaffolding structure 751 or mesh and formed into a tube having a substantially cylindrical shape with a lumen therethrough. The scaffolding structure 751 may be constructed of a memory material, such as Nitinol®, including ASTM F2063.

The thickness of the scaffolding structure 751 may be between about 0.30 mm and about 0.60 mm. In other embodiments, the thickness of the scaffolding structure 751 may be between about 0.35 mm and about 0.55 mm. In other embodiments, the thickness of the scaffolding structure 751 may be between about 0.40 mm and about 0.50 mm. In other embodiments, the thickness of the scaffolding structure 751 may be about 0.45 mm.

As illustrated best in FIG. 7A, the scaffolding structure 751 may be formed of multiple annular segments 752 (or rings) disposed on a circumference and defining at least a portion of the generally cylindrical shape of the scaffolding structure 751. Each annular segment 752 may comprise a plurality of interconnected strut arms 753. For example, the strut arms 753 may be connected such that they form a zigzag pattern, defining alternating "peaks" and "valleys," around the annular segment 752. (As used herein, "peaks"

refer to the relative high points and "valleys" refer to the relative low points where strut arms 753, arranged in a zigzag pattern, connect. In other words, the peaks and valleys may be relative to one end 754, 755 of the stent 750, rather than relative to the circumference of the stent 750.) In some embodiments adjacent strut arms 753 may form acute angles relative to each other.

The adjacent annular segments 752 may be arranged in rows around a longitudinal axis $A_L$ of the generally cylindrical shape of the scaffolding structure 751. The rows may be arranged in the longitudinal direction of the generally cylindrical shape of the scaffolding structure 751. Adjacent annular segments 752 may be coupled to each other by connectors 756.

The components and elements of the scaffolding structure 751, including the annular segments 752, the strut arms 753, and the connectors 756, may be configured to balance transverse forces applied to the scaffolding structure 751, for example, to reduce the incidence of infolding. The components and elements of the scaffolding structure 751 may be configured to allow at least a portion of the scaffolding structure 751 to decrease in diameter in response to an axial force applied to the scaffolding structure 751, for example to enable sheathing of the stent 750 in a deployment device and/or retrieval of the stent 750.

Some example embodiments of a scaffolding structure 751 are disclosed in U.S. patent application Ser. No. 10/288,615 (issued as U.S. Pat. No. 7,527,644) and U.S. patent application Ser. No. 13/285,358, which are hereby incorporated herein by reference in their entirety.

As will be appreciated, the entire stent 750 may be defined by an integrally formed scaffolding structure 751. In other embodiments, the scaffolding structure 751 may form merely a portion of the stent 750, such as all or a portion of a proximal region (or a mid-body) and/or all or a portion of a distal region (or a flared region), and other portions of the stent 750 may be formed by another structure and/or material, such as woven Nitinol® wire mesh that may be coupled to the laser cut scaffolding structure 751 through a winding or weaving process.

The scaffolding structure 751 may be coated, or otherwise be enclosed in a cover 760 formed of a flexible material. The cover 760 may be elastomeric, polymeric, or comprised of any other material known in the art. In some embodiments, the cover 760 may include polyurethane, while in certain embodiments the cover may be comprised only of polyurethane. In some embodiments, the cover 760 may include silicone, while in certain embodiments the cover may be comprised only of silicone. In some embodiments, an internal surface of the cover may be coated with a hydrophilic layer. Some example embodiments of coverings are disclosed in U.S. patent application Ser. No. 10/669,450 (issued as U.S. Pat. No. 7,637,942), U.S. patent application Ser. No. 10/718,217 (issued as U.S. Pat. No. 7,959,671), and U.S. patent application Ser. No. 12/616,455 (issued as U.S. Pat. No. 8,206,436), all of which are hereby incorporated herein by reference in their entirety.

As further shown in FIG. 7A, the valve 700 may be coupled to an inside diameter or inner lumen of the stent 750. Thus, the valve 700 is not directly visible in the illustrated embodiment of FIG. 7A, though its position is indicated by a reference line. A stitching element 765 such as a suture may be used to secure the valve 700 to the inner diameter of the stent 750. For example, the stitching element 765 may secure the valve 700 to strut arms 753 of the scaffolding structure 751 of the stent 750. In another embodiment, the stitching element 765 may secure the valve 700 to the cover 760 of the stent 750. The stitching element 765 may further be configured and/or positioned to pass through the rim and the reinforcement member of the valve 700. In another embodiment, a plurality of ties may be used to secure the valve 700 to the inner diameter of the stent 750.

In the case of esophageal stents, the valve 700 may be positioned such that the opening is disposed at the distal end of the valve 700 toward the stomach while the rim is disposed at the proximal end of the valve 700 toward the mouth. In this orientation, the valve 700 may more readily open to allow food to pass to the stomach, but generally will prevent reflux from the stomach, except in response to a relatively large force—for instance when a patient belches or vomits.

FIG. 7B shows a cross-sectional view of the stent 750 of FIG. 7A taken along the view line 7B. As shown therein, the stent 750 is configured such that the valve 700 is coupled to its inner diameter.

Figure 8A:
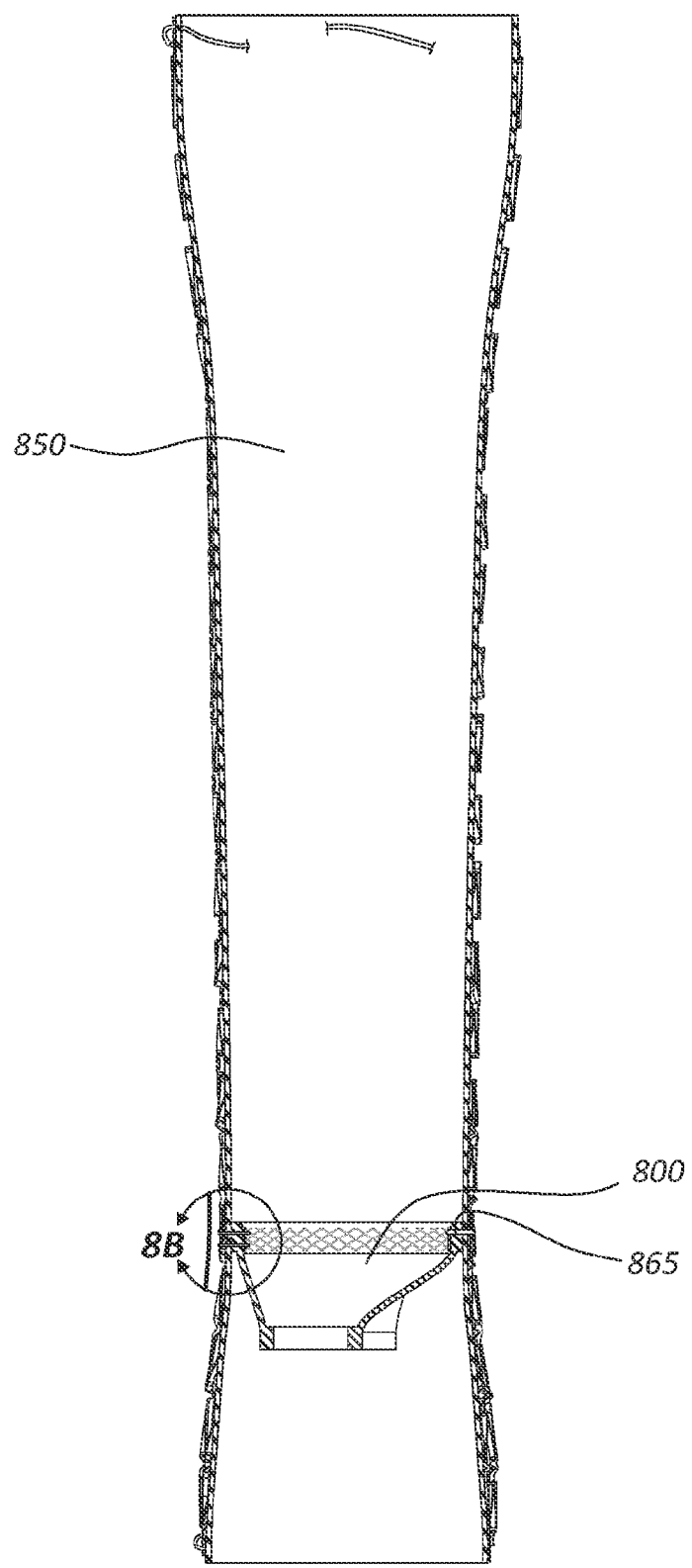
FIG. 8A is a cross-sectional view of a stent incorporating a valve, according to an embodiment of the present disclosure.
Figure 8B:
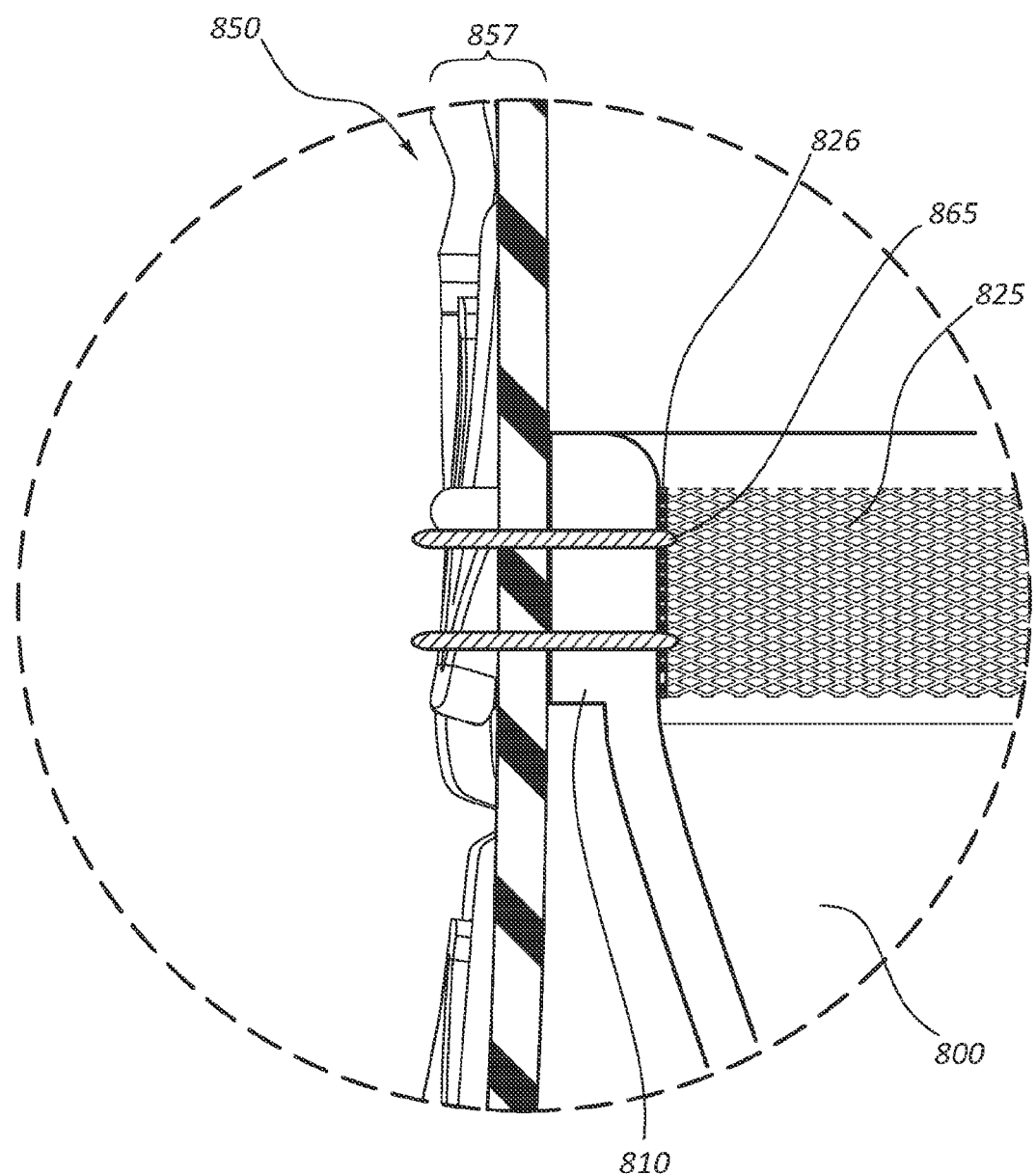
FIG. 8B is an enlarged view of a portion of the stent of FIG. 8A taken along the view line 8B.

FIG. 8A shows a cross-sectional view of a stent 850 configured with a valve 800 according to the present disclosure. As shown therein, the valve 800 may be coupled to the inner diameter of the stent 850 by a stitching element 865. FIG. 8B is a close-up of a portion of the stent of FIG. 8A. As shown therein, the stitching element 865 may be configured such that it passes through a wall 857 of the stent 850 and the rim 810 of the valve 800. The stitching element 865 may further pass through the reinforcement member 825. In some embodiments, the stitching element 865 may be secured to or otherwise wrapped around the individual threads or wires 826 of the reinforcement member 825. Thus, the reinforcement member 825 may aid in preventing the stitching element 865 from tearing through the rim 810 of the valve 800.

Additional ways of reinforcing the valve are also disclosed herein. For example, in some embodiments, the individual leaflets may be coupled to one another at one or more locations along the perimeter of the opening of the valve. The one or more locations at which the individual leaflets couple to one another may be relatively weak and susceptible to tearing after repeatedly transitioning the valve between the closed configuration and the antegrade and/or retrograde open configurations. In some embodiments, it may therefore be desirous to reinforce and/or strengthen the one or more locations at which the individual leaflets couple to one another. This reinforcement and/or strengthening may be accomplished in a variety of ways. In some embodiments, a manufacturing technique may be used in forming the valve that is capable of providing a relatively smooth surface at the one or more locations. In other embodiments, a manufacturing technique may be used in forming the valve that does not require cutting the valve at or near the one or more locations. In still other embodiments, the one or more locations may be reinforced and/or strengthened by localized thickening of the leaflets.

Disclosed herein are also methods of forming a valve. A variety of materials may be used in forming the valve. For example, the body, the rim, and the opening may comprise a polymeric or elastomeric material. In some embodiments, the polymeric or elastomeric material may be viscoelastic. In some embodiments, the polymeric or elastomeric material may be relatively soft. The polymeric or elastomeric material may also be relatively flexible such that the shape of the valve may be altered (e.g., stretched or compressed) without inflicting damage to the valve.

Materials having a broad range of percent elongation may be used. In some embodiments, it is desirous that the polymeric or elastomeric material have a percent elongation of between about 50% and about 3000%. In other embodiments, the polymeric or elastomeric material has a percent elongation of between about 500% and about 2500%. In yet other embodiments, the polymeric or elastomeric material has a percent elongation of between about 1000% and about 2000%.

Materials having a variety of tensile strengths may be used. For example, in some embodiments, the polymeric or elastomeric material has a tensile strength of between about 0.01 MPa and about 5 MPa. In other embodiments, the polymeric or elastomeric material has a tensile strength of between about 1 MPa and about 4 MPa. In yet other embodiments, the polymeric or elastomeric material has tensile strength of between about 2 MPa and about 3 MPa.

In some embodiments, the material may comprise an open cell foam. The physical characteristics and properties of the foam may be configured as desired. For example, in some embodiments, the foam may comprise a Young's Modulus of between about 0.1 MPa and about 0.6 MPa. In other embodiments, the foam may comprise a Young's Modulus of between about 0.2 MPa and about 0.5 MPa. In yet other embodiments, the foam may comprise a Young's Modulus of between about 0.3 MPa and about 0.4 MPa.

The density of the foam may also vary. For example, in some embodiments, the density of the foam may be between about 0.1 g/cm$^3$ and about 1.5 g/cm$^3$. In other embodiments, the density of the foam may be between about 0.3 g/cm$^3$ and about 1.2 g/cm$^3$. In yet other embodiments, the density of the foam may be between about 0.5 g/cm$^3$ and about 0.9 g/cm$^3$. In yet other embodiments, the density of the foam may be between about 0.6 g/cm$^3$ and about 0.8 g/cm$^3$. In yet other embodiments, the density of the foam may be between about 0.5 g/cm$^3$ and about 0.6 g/cm$^3$. In yet other embodiments, the density of the foam may be between about 0.8 g/cm$^3$ and about 0.9 g/cm$^3$.

The material used for the production of the valve may also comprise additional agents and/or additives that may provide the valve with added properties or benefits. For example, in some embodiments, the material may be treated with an antimicrobial agent to prevent or limit the growth of microorganisms when the valve is disposed within, for example, the esophagus of a patient.

Also disclosed herein are methods of manufacturing a stent or another implantable device that may be disposed within a body lumen. The method may comprise a step of obtaining a substantially cylindrical-shaped metal stent. The method may further comprise a step of obtaining a valve. As set forth above, the valve may comprise a body, a substantially cylindrical-shaped rim, an opening, and a reinforcement member. The method may further comprise a step of coupling the valve to an inner lumen of the substantially cylindrical stent via a stitching element. The stitching element may be disposed through the reinforcement member of the valve. Further, in some embodiments, the method may comprise a step of coupling the reinforcement member to the substantially cylindrical-shaped rim prior to coupling the valve to the inner lumen of the substantially cylindrical stent.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

What is claimed is:

1. A valve for placement in a body lumen, comprising:
   a body;
   a substantially cylindrical-shaped rim disposed at a first end of the valve, the substantially cylindrical-shaped rim having a proximal end and a distal end;
   an opening disposed at a second end of the valve, wherein the opening comprises one or more leaflets, the opening having a closed configuration in which the leaflets are closed, an antegrade open configuration in which the leaflets are opened in response to an antegrade force, and a retrograde open configuration in which the leaflets are opened in response to a retrograde force; and
   a reinforcement member molded within the substantially cylindrical-shaped rim, the reinforcement member being constrained to the substantially cylindrical-shaped rim such that the reinforcement member is disposed between the proximal end and the distal end of the substantially cylindrical-shaped rim, the reinforcement member comprising a mesh material having a plurality of openings configured to receive a stitching element, wherein the reinforcement member is configured to prevent the stitching element from tearing through the substantially cylindrical-shaped rim in response to the antegrade force and the retrograde force, and wherein the reinforcement member is formed from a different material than the substantially cylindrical-shaped rim.

2. The valve of claim 1, wherein the opening comprises at least three leaflets.

3. The valve of claim 1, wherein the reinforcement member is disposed adjacent an inner diameter of the substantially cylindrical-shaped rim.

4. The valve of claim 1, wherein the reinforcement member is disposed adjacent an outer diameter of the substantially cylindrical-shaped rim.

5. The valve of claim 1, wherein the tear strength of the reinforcement member is greater than the tear strength of the material used to form the substantially cylindrical-shaped rim.

6. The valve of claim 1, wherein the body comprises an inner surface and an outer surface, wherein, in the closed configuration, the inner surface is substantially concave and the outer surface is substantially convex.

7. The valve of claim 1, wherein the body comprises an inner surface and an outer surface, wherein, in the antegrade open configuration, the inner surface is substantially concave and the outer surface is substantially convex.

8. The valve of claim 1, wherein the body comprises an inner surface and an outer surface, wherein, in the retrograde open configuration, the inner surface is substantially convex and the outer surface is substantially concave.

9. The valve of claim 1, wherein the body of the valve is inverted in the retrograde open configuration.

10. The valve of claim 1, wherein the mesh material has a density of between about 135 ends per inch and about 425 ends per inch.

11. An implantable device to be disposed within a body lumen, the implantable device comprising:
    a substantially cylindrical-shaped stent having an inner lumen extending therethrough; and a two-way valve configured to allow passage of flow in both an antegrade direction and a retrograde direction, the two-way valve comprising a body, a substantially cylindrical-shaped rim, an opening, and a reinforcement member comprising a mesh material formed from a plurality of threads, the reinforcement member being molded within the substantially cylindrical-shaped rim, wherein the tear strength of the reinforcement member is greater than the tear strength of the material used to form the substantially cylindrical-shaped rim;

wherein the two-way valve is coupled to the inner lumen of the substantially cylindrical-shaped stent by a stitching element, the stitching element passing through each of a wall of the substantially cylindrical-shaped stent, the substantially cylindrical-shaped rim of the valve, and between a portion of the plurality of threads forming the mesh material of the reinforcement member such that the stitching element is prevented from tearing through the substantially cylindrical-shaped rim upon passage of flow through the two-way valve in the antegrade direction and the retrograde direction.

12. The implantable device of claim 11, wherein the reinforcement member is disposed adjacent an inner diameter of the substantially cylindrical-shaped rim.

13. The implantable device of claim 11, wherein the reinforcement member is disposed adjacent an outer diameter of the substantially cylindrical-shaped rim.

14. The implantable device of claim 11, wherein the substantially cylindrical-shaped rim has a proximal end and a distal end, and wherein the opening comprises one or more leaflets, the opening having a closed configuration in which the leaflets are closed, an antegrade open configuration in which the leaflets are opened in response to an antegrade force, and a retrograde open configuration in which the leaflets are opened in response to a retrograde force.

15. The implantable device of claim 11, wherein the mesh material has a density of between about 135 ends per inch and about 425 ends per inch.

16. A method of making an implantable device to be disposed within a body lumen, the method comprising:
obtaining a substantially cylindrical-shaped stent, the substantially cylindrical-shaped stent having an inner lumen extending therethrough;
obtaining a two-way valve configured to allow passage of flow in both an antegrade direction and a retrograde direction, wherein the two-way valve comprises a body, a substantially cylindrical-shaped rim, an opening, and a reinforcement member comprising a mesh material formed from a plurality of threads having a density of between about 135 ends per inch and about 425 ends per inch, the reinforcement member being molded within the substantially cylindrical-shaped rim, the reinforcement member being constrained to the substantially cylindrical-shaped rim such that the reinforcement member is disposed between a proximal end and a distal end of the substantially cylindrical-shaped rim, wherein the reinforcement member is formed from a different material than the substantially cylindrical-shaped rim; and
coupling the two-way valve to the inner lumen of the substantially cylindrical-shaped stent via a stitching element disposed through the substantially cylindrical-shaped stent, the substantially cylindrical-shaped rim of the valve, and a portion of the plurality of threads forming the mesh material of the reinforcement member of the two-way valve such that the stitching element is prevented from tearing through the substantially cylindrical-shaped rim upon passage of flow through the two-way valve in the antegrade direction and the retrograde direction.

17. The method of claim 16, further comprising:
molding the reinforcement member within the substantially cylindrical-shaped rim prior to coupling the valve to the inner lumen of the substantially cylindrical-shaped stent.

18. A stent to be disposed within a body lumen, the stent comprising:
a scaffolding structure formed into a tube having a substantially cylindrical shape, the scaffolding structure having an inner lumen extending therethrough; and
a valve comprising:
a body;
a substantially cylindrical-shaped rim disposed at a first end of the body, the substantially cylindrical-shaped rim having a proximal end and a distal end;
an opening disposed at a second end of the body, wherein the opening comprises one or more leaflets, the opening having a closed configuration in which the leaflets are closed, an antegrade open configuration in which the leaflets are opened in response to an antegrade force, and a retrograde open configuration in which the leaflets are opened in response to a retrograde force; and
a reinforcement member comprising a mesh material having a density of between about 135 ends per inch and about 425 ends per inch, the reinforcement member molded within the substantially cylindrical-shaped rim, the reinforcement member being constrained to the substantially cylindrical-shaped rim such that the reinforcement member is disposed between the proximal end and the distal end of the substantially cylindrical-shaped rim, wherein the reinforcement member is formed from a different material than the substantially cylindrical-shaped rim, and wherein the tear strength of the reinforcement member is greater than the tear strength of the material used to form the substantially cylindrical-shaped rim;
wherein the valve is coupled to the inner lumen of the scaffolding structure by a stitching element disposed through a plurality of openings of the mesh material of the reinforcement member, the mesh material configured to prevent the stitching element from tearing through the substantially cylindrical-shaped rim in response to the antegrade force and the retrograde force.

* * * * *